(12) United States Patent
Wellstein et al.

(10) Patent No.: US 6,245,748 B1
(45) Date of Patent: Jun. 12, 2001

(54) INHIBITION OF AN FGF-BINDING PROTEIN USING RIBOZYMES

(75) Inventors: Anton Wellstein, Washington, DC (US); Frank Czubayko, Betehsda, MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/160,588

(22) Filed: Sep. 25, 1998

Related U.S. Application Data

(60) Provisional application No. 60/060,170, filed on Sep. 26, 1997.

(51) Int. Cl.[7] .................................................. A01N 43/04
(52) U.S. Cl. ........................... 514/44; 435/6; 435/91.31; 435/325; 435/375; 536/23.1; 536/23.2; 536/24.5
(58) Field of Search ........................... 514/44; 424/93.21; 435/7.23, 375, 320.1, 91.31, 6, 325; 536/23.2, 23.1, 24.5, 24.3

(56) References Cited

PUBLICATIONS

Crooke, S., Basic Principles of Antisense Therapeutics, Springer–Verlag Berlin Heidelberg New York, Jul. 1998.*
Gura T., Antisense Has Growing Pains, Science, vol. 270, pp. 575–577, Oct. 1995.*
Crooke, S. et al., Antisense '97: A roundtable on the state of the industry, Nature Biotechnology, vol. 15, p. 522, Jun. 1997.*
Branch, A., A good antisense molecule is hard to find, TIBS vol. 23, pp 47–49, Feb. 1998.*
Czubayako et al., "A Secreted FGF–Binding Protein Can Serve As The Angiogenic Switch In Human Cancer," Nature Medicine, 3: 1137–1140 (1997).
Czubayako et al., "Ribozyme–Targeting Elucidates A Direct Role Of Pleiotrophin In Tumor Growth," The Journal of Biological Chemistry, 269: 21358–21363 (1994).
Czubayako et al., "Tumor Growth And Angiogenesis Induced By A Secreted Binding Protein For Fibroblast Growth Factors," The Journal of Biological Chemistry, 269: 28243–28248 (1994).
Harris et al., "Phorbol Ester–Induced Transcription Of A Fibroblast Growth Factor–Binding Protein Is Modulated By A Complex Interplay Of Positive And Negative Regulatory Promoter Elements," The Journal of Biological Chemistry, 273: 19130–19139 (1998).
Wu et al., "Characterization And Molecular Cloning Of A Positive Binding Protein For Heparin–Binding Growth Factors," The Journal of Biological Chemistry, 266: 16778–16785 (1991).

* cited by examiner

Primary Examiner—Robert A. Schwartzman
Assistant Examiner—Janet Epps
(74) Attorney, Agent, or Firm—Robin L. Teskin

(57) ABSTRACT

Increased expression of a secreted FGF-binding protein (FGF-BP) occurs in certain autoimmune and malignant disease conditions. It is found, for example, that tumor secretions of FGF-BP results in mobilization and activation of locally-stored FGFs that can serve as an angiogenic switch molecule. Furthermore, it has been found that in an animal model of multiple sclerosis (MS), the exacerbation of the disease is accompanied by increased FGF-BP. Using ribozymes, it is possible to cause cleavage of the FGF-BP mRNA. Hence, administration of ribozymes which cleave the FGF-BP mRNA in sufficient amounts to inhibit disease processes triggered by FGF-BP is appropriate.

14 Claims, 1 Drawing Sheet

SEQUENCE LISTING

<160> NUMBER OF SEQ ID NOS: 5

<210> SEQ ID NO: 1
<211> LENGTH: 1163
<212> TYPE: DNA
<213> ORGANISM: Homo sapiens

<400> SEQUENCE: 1

```
ctctacctga cacagctgca gcctgcaatt cactcccact gcctgggatt gcactggatc      60
cgtgtgctca gaacaaggtg aacgcccagc tgcagccatg aagatctgta gcctcaccct     120
gctctccttc ctcctactgg ctgctcaggt gctcctggtg gagggaaaa aaaaagtgaa     180
gaatggactt cacagcaaag tggtctcaga acaaaaggac actctgggca acacccagat     240
taagcagaaa agcaggcccg ggaacaaagg caagtttgtc accaaagacc aagccaactg     300
cagatgggct gctactgagc aggaggaggg catctctctc aaggttgagt gcactcaatt     360
ggaccatgaa ttttcctgtg tctttgctgg caatccaacc tcatgcctaa agctcaagga     420
tgagagagtc tattggaaac aagttgcccg gaatctgcgc tcacagaaag acatctgtag     480
atattccaag acagctgtga aaaccagagt gtgcagaaag gattttccag aatccagtct     540
taagctagtc agctccactc tatttgggaa cacaaagccc aggaaggaga aaacagagat     600
gtcccccagg gagcacatca agggcaaaga gaccaccccc tctagcctag cagtgaccca     660
gaccatggcc accaaagctc ccgagtgtgt ggaggaccca gatatggcaa accagaggaa     720
gactgccctg gagttctgtg gagagacttg gagctctctc tgcacattct tcctcagcat     780
agtgcaggac acgtcatgct aatgaggtca aaagagaacg ggttcccttta agagatgtca     840
tgtcgtaagt ccctctgtat actttaaagc tctctacagt ccccccaaaa tatgaacttt     900
tgtgcttagt gagtgcaacg aaatatttaa acaagtttg tattttttgc ttttgtgttt     960
tggaatttgc cttatttttc ttggatgcga tgttcagagg ctgtttcctg cagcatgtat    1020
ttccatggcc cacacagcta tgtgtttgag cagcgaagag tctttgagct gaatgagcca    1080
gagtgataat ttcagtgcaa cgaactttct gctgaattaa tggtaataaa actctgggtg    1140
tttttcaaaa aaaaaaaaaa aaa                                            1163
```

-continued

```
<210> SEQ ID NO: 2
<211> LENGTH: 16
<212> TYPE: DNA
<213> ORGANISM: Artificial Sequence
<220> FEATURE:
<223> OTHER INFORMATION: Description of Artificial Sequence: Ribozyme
      target site

<400> SEQUENCE: 2
gtgcactcaa ttggac                                               16

<210> SEQ ID NO: 3
<211> LENGTH: 16
<212> TYPE: DNA
<213> ORGANISM: Artificial Sequence
<220> FEATURE:
<223> OTHER INFORMATION: Description of Artificial Sequence: Ribozyme
      target site

<400> SEQUENCE: 3
agagagtcta ttggaa                                               16

<210> SEQ ID NO: 4
<211> LENGTH: 16
<212> TYPE: DNA
<213> ORGANISM: Artificial Sequence
<220> FEATURE:
<223> OTHER INFORMATION: Description of Artificial Sequence: Ribozyme
      target site

<400> SEQUENCE: 4
gacacgtcat gctaat                                               16

<210> SEQ ID NO: 5
<211> LENGTH: 16
<212> TYPE: DNA
<213> ORGANISM: Artificial Sequence
<220> FEATURE:
<223> OTHER INFORMATION: Description of Artificial Sequence: Ribozyme
      target site

<400> SEQUENCE: 5
cgtaagtccc tctgta                                               16
```

INHIBITION OF AN FGF-BINDING PROTEIN USING RIBOZYMES

This application claims benefit of provisional application Ser. No. 60/060,170 filed Sep. 26, 1997.

FIELD OF THE INVENTION

This invention relates to use of ribozymes for inhibition of fibroblast growth factor binding protein (FGF-BP). The increase of FGF-BP is accompanied by various pathological changes, including the disease phenomena seen in autoimmune disease, e.g., multiple sclerosis and in growth and metastatic spread of cancer.

BACKGROUND OF THE INVENTION

Fibroblast growth factor (FGF) is a potentially active growth factor found in large amounts in the nervous system and, to a somewhat lesser extent, in the rest of the body. Because of the blood-brain barrier, the two reservoirs, including the components such as the FGF and FGF-binding protein, remain separated. However, in certain instances of infection or trauma there is cross-over between the two reservoirs.

Tumor growth and, ultimately, metastasis is a complex process regulated in part by factors controlling cellular proliferation and death as well as tumor angiogenesis. The driving factors which regulate angiogenesis and tumor growth need to be understood to control the process of growth in malignancies. It is known that tumor cells and their normal stroma express a multitude of candidate angiogenic factors. Very few specific inhibitors have been generated to assess which of these gene products are only innocent bystanders and which contribute significantly to tumor angiogenesis and metastasis.

Developmental expression of the retinoid-regulated FGF-BP gene is prominent in the skin and intestine during the perinatal phase and is down-modulated in the adult. The gene is, however, up-regulated in various cancers such as carcinogen-induced skin tumor, in squamous cell carcinoma, in breast cancers and in some colon cancer cell lines and tumor samples. FGF-BP is also up-regulated in autoimmune responses of the nervous system such as in the case of multiple sclerosis.

Tumor-angiogenesis, a process whereby factors stimulating the ingrowth of blood vessels into the tumor are secreted into the local tumor milieu by cancer and stroma cells, also plays a critical role by regulating the balance between cell proliferation and cell death and by providing a route for distant spread. Both clinical and laboratory evidence suggest that spread of malignant cells from a localized tumor is directly related to the number of microvessels in the primary tumor. Of the multitude of factors secreted by tumor and stroma cells which are potentially angiogenic, two have been confirmed as angiogenic factors which are rate-limiting in in vivo tumor models. The importance of one of these, vascular endothelial growth factor/vascular permeability factors (VEGF/VPF), was previously demonstrated through functional knockout through use of blocking antibodies. A critical role for the other factor, pleotrophin (PTN), has been shown in angiogenesis and metastasis associated with melanoma using a hammerhead-ribozyme PTN mRNA depletion strategy.

SUMMARY OF THE INVENTION

It has now been discovered that increased expression of a secreted FGF-binding protein (FGF-BP) occurs in certain autoimmune and malignant disease conditions. It is found, for example, that tumor secretions of FGF-BP results in mobilization and activation of locally-stored FGFs that can serve as an angiogenic switch molecule. Furthermore, it has been found that in an animal model of multiple sclerosis (MS), the exacerbation of the disease is accompanied by increased FGF-BP. Using ribozymes, it is possible to cause cleavage of the FGF-BP mRNA. Hence, administration of ribozymes which cleave the FGF-BP mRNA in sufficient amounts to inhibit disease processes triggered by FGF-BP is appropriate.

DESCRIPTION OF THE INVENTION

Figure 1:
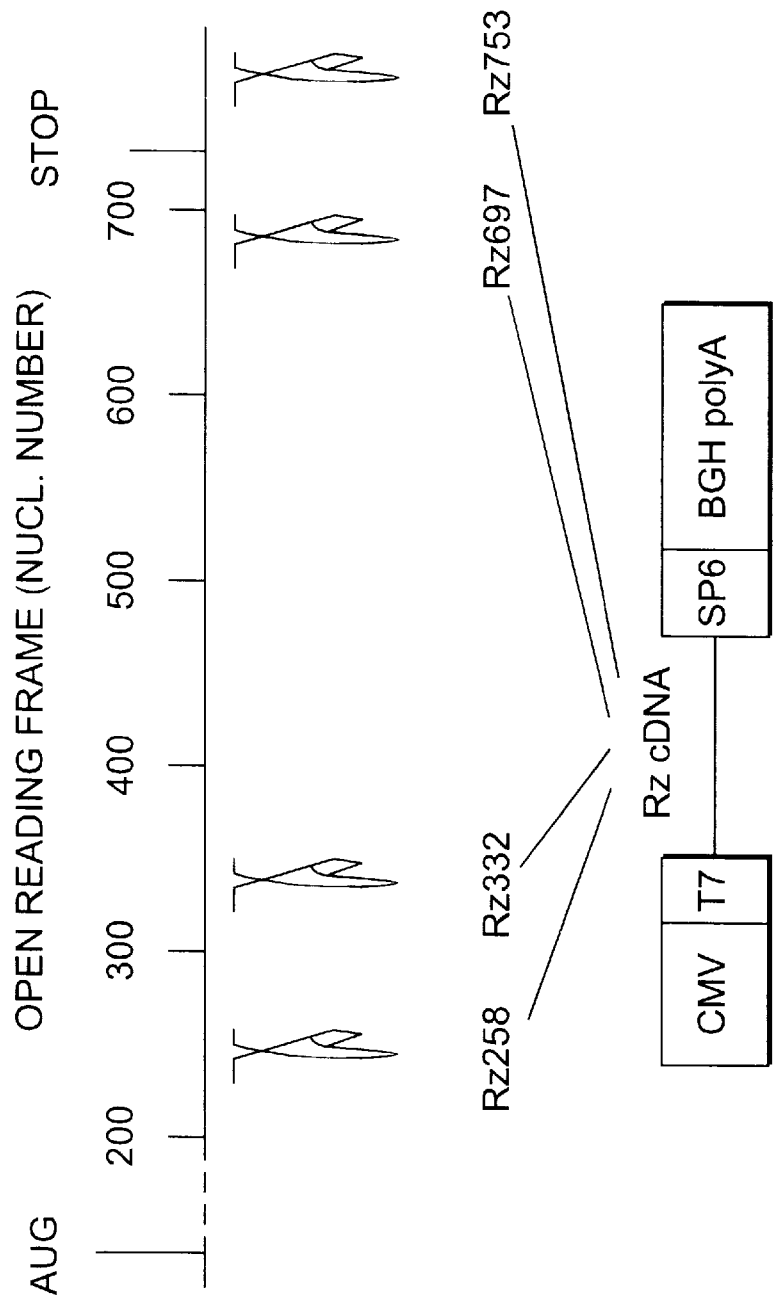
FIG. 1 shows the ribozyme target sites, expression vector and in vitro cleavage of FGF-BP mRNA.

It has now been found that expression of FGF-binding protein (FGF-BP) causes mobilization and activation of locally stored FGFs that can serve as switch molecules. The FGF-BP expression can be controlled by targeting with ribozymes, thereby reducing the FGF-BP release of biologically active bFGF from cells. Furthermore, the growth and angiogenesis of tumors can be decreased in parallel with the reduction of FGF-BP. Additionally, it now is seen that autoimmune responses can be modulated by reducing FGF-BP release using the methods of the invention.

Materials and Methods

Generation of Constructs

The FGF-BP expression vector containing the open reading frame (ORF) of FGF-BP from −42 to +707 (with A in the translation initiation codon being +1, Genebank #M60047) was previously described (Czubayko, et al., *J. Biol. Chem.* 269:28243–28248 (1994)). The FGF-BP-targeted ribozymes were designed to cleave 258, 332, 697 or 753 downstream of the translation initiation site (FIG. 1). The PCR product was purified using the ion exchange columns and reagents purchased from Qiagen (Chatsworth, Calif.). The product of the PCR reaction was digested in HindIII and XbaI and cloned into pRc/CMV expression vector purchased from Invitrogen. All of the ribozymes exemplified have 8 nucleotides of 5' and 3' flanking antisense sequence stretches to direct them to the predicted cleavage site. Synthetic sense and antisense oligonucleotides containing the catalytic center and the flanking regions of each of the ribozymes were annealed and ligated as described earlier. (See Czubayko, et al., *J. Biol. Chem.* 269, 21358–21363 (1994)).

The mRNA sequence giving rise to FGF-BP as recorded in the gene bank is of the formula: SEQ ID NO: 1

| 1 | ctctacctga | cacagctgca | gcctgcaatt | cactcccact | gcctgggatt |
|---|---|---|---|---|---|
|  | gcactggatc |  |  |  |  |
| 61 | cgtgtgctca | gaacaaggtg | aacgcccagc | tgcagccatg | aagatctgta |
|  | gcctcaccct |  |  | ↑ |  |

-continued

| | | | | |
|---|---|---|---|---|
| 121 gctctccttc aaaaagtgaa | ctcctactgg | ctgctcaggt | gctcctggtg | gaggggaaaa |
| 181 gaatggactt acacccagat | cacagcaaag | tggtctcaga | acaaaaggac | actctgggca |
| 241 taagcagaaa aagccaactg | agcaggcccg | ggaacaaagg | caagtttgtc | accaaagacc |
| 301 cagatgggct gcactcaatt | gctactgagc | aggaggaggg | catctctctc | aaggttgagt |
| 361 ggaccatgaa agctcaagga | tttcctgtg | tctttgctgg | caatccaacc | tcatgcctaa |
| 421 tgagagagtc acatctgtag | tattggaaac | aagttgcccg | gaatctgcgc | tcacagaaag |
| 481 atattccaag aatccagtct | acagctgtga | aaaccagagt | gtgcagaaag | gattttccag |
| 541 taagctagtc aaacagagat | agctccactc | tatttgggaa | cacaaagccc | aggaaggaga |
| 601 gtcccccagg cagtgaccca | gagcacatca | agggcaaaga | gaccaccccc | tctagcctag |
| 661 gaccatggcc accagaggaa | accaaagctc | ccgagtgtgt | ggaggaccca | gatatggcaa |
| 721 gactgccctg tcctcagcat | gagttctgtg | gagagacttg | gagctctctc | tgcacattct |
| 781 agtgcaggac agagatgtca | acgtcatgct | aatgaggtca | aaagagaacg | ggttccttta |
| 841 tgtcgtaagt tatgaacttt | ccctctgtat | actttaaagc | tctctacagt | cccccaaaa |
| 901 tgtgcttagt ttttgtgttt | gagtgcaacg | aaatatttaa | acaagttttg | tattttttgc |
| 961 tggaatttgc cagcatgtat | cttatttttc | ttggatgcga | tgttcagagg | ctgtttcctg |
| 1021 ttccatggcc gaatgagcca | cacacagcta | tgtgtttgag | cagcgaagag | tctttgagct |
| 1081 gagtgataat actctgggtg | ttcagtgcaa | cgaactttct | gctgaattaa | tggtaataaa |
| 1141 ttttcaaaa | aaaaaaaaaa | aaa | | | wherein ↑ identifies the beginning of the coding sequence. (The identification of the sequence chosen as a target sequence relates to the number attributed to the position with relation to the beginning of the coding sequence, and not with relation to the number appearing on the right hand side of the listings.)

Cell Lines, Transfections and Growth Assays

SW-13, LS174T and ME-180 cells (obtained from American Type Culture Collection (ATCC), Rockville, Md.) were cultured in IMEM with 10% fetal calf serum. Cells were transfected at 50% confluency for 5 hours with 20 μg of plasmid DNA mixed with 140 μl of LIPOFECTAMINE™ in serum-free OPTIMEM™ medium (Life Technologies) at 37° C. with 5% $CO_2$. The transfection medium was then replaced with fresh medium and, 36 hours later, G418 at 50 μg/ml (SW-13, LS174T) or at 1000 μg/ml (ME-180) was added to select stably transfected cells for another 6–8 weeks. Studies of anchorage-independent growth of transfected SW-13 cells were carried out as described previously by Fang, et al. (J. Biol. Chem 267, 25889–25897 (1992)).

Detection of FGF-BP mRNA by Northern Blot

Total RNAs from cell lines or tumor tissues were isolated, blotted and quantitated using a random primed FGF-BP cDNA probe. FGF-BP transcript was quantitated after phosphorimaging and probing for loading with GAPDH. (See Liaudet-Coopman, et al., *J. Biol. Chem.* 271, 21303–21308 (1996)).

Staining for Basic FGF

Cells were plated overnight, washed, three times with PBS, fixed in 3.7% formaldehyde/0.1% Triton X-10 for 10 minutes, washed again in PBS and then incubated for 20 minutes at room temperature with a 1:2000 dilution of rabbit anti-bFGF antibody in PBS. After a further triplicate wash in PBS, bound antibody was detected by fluorescence of rhodamine-labeled mouse anti-rabbit IgG (Boehringer Mannheim).

Detection of FGF-BP Protein

Serum-free media conditioned overnight by the different cell lines at approximately 80% confluency were harvested and proteins present in 500 μl of undiluted, and PBS-diluted (1:3, 1:10 and 1:30) conditioned media were immobilized by micro-filtration onto nitrocellulose membrane a dotblot apparatus (Biorad). After washing in Tris-buffered saline, (TBS) and blocking of free sites with 5% skim milk, affinity-purified rabbit IgG raised against a human FGF-PB/GST fusion protein was used for detection of the immobilized antigen with an ECL detection assay (Amersham).

Ribozyme sites were numbered according to their cleavage sites relative to the translation start site in the FGF-BP mRNA. Ribozyme target sites were of the formulas:

(258) gtgcactcaattggac SEQ ID NO: 2
(332) agagagtctattggaa SEQ ID NO: 3
(697) gacacgtcatgctaat SEQ ID NO: 4
(753) cgtaagtccctctgta SEQ ID NO: 5

The ribozyme directed against SeQ. 5 (a non-translational region) were not effective.

Ribozyme expression vectors were generated and evaluated for in vitro catalytic activity. Ribozyme expression was under the control of a CMV promotor. Each of the individual ribozymes, as well as a multimerized construct containing all of the ribozymes in tandem, were found to cleave the FGF-BP mRNA at the predicted cleavage sites. After in vitro run-off transcription using T7 polymerase, $^{32}$P-labeled FGF-BP transcripts were incubated with unlabeled ribozyme transcripts for different times and the resulting products were separated on a polyacrylamide gel. The expected sizes of the intact FGF-BP transcript (812 nts) and the cleavage products (491 and 321 nts) obtained with Rz258 were noted of particular interest.

While the ribozymes tested were 16 bases in length, ribozymes of 8 to 30 bases targeting any of the transcriptional mRNA would be suggested as useful, with ribozymes of 16 to 20 bases are preferred.

To assess the in vivo efficacy of the ribozyme constructs, the targeted FGF-BP was expressed (alone or in combination with different ribozyme constructs) by stable transfection of FGF-BP-negative SW-13 cells. More specifically, SW-13 cells were stably transfected with an expression vector for FGF-BP (5 µg) and the different ribozyme expression vectors or the empty vector (20 µg) (The Rz753 is targeted to the 3'-untranslated region not included in the expression vector, and could serve as an additional negative control.) It was found that co-transfection of ribozymes Rz258, Rz697 or Rz332 was effective in reducing transcript levels of the transfected gene. A multimerized ribozyme construct containing all ribozymes in tandem had similar efficacy.

In a bioassay to study effects of ribozyme-targeting, it was found that soft agar colony formation of the FGF-BP-transfected SW-13 cells was prevented by co-expression of Rz258, Rz697 or Rz332. In addition, bFGF release for FGF-BP-transfected cells was reduced to background levels and tumorigenicity in nude mice was reversed upon co-transfection of these ribozyme constructs. It was also shown that Rz753 served as an additional negative control, since its target sequence in the 3'-UTR is not contained in the FGF-BP expression vector. Indeed, co-transfection with expression vector Rz753 did not affect the in vitro or in vivo phenotype of the FGF-BP-transfected SW-13 cells.

To evaluate the FGF-BP as a potential angiogenic switch for squamous cell carcinoma (SCC), endogenous FGF-BP in human ME-180 cells was reduced to varying residual levels using Rz332 and Rz697. These two ribozymes were selected because the target site of Rz258 is very close to Rz332 and both ribozymes had been equally effective in the previous studies. As shown on Northern blot, Rz332 and Rz697 decreased FGF-BP mRNA significantly by 57% and 20%, respectively (p<0.001). Quantitative slot blots revealed a similar reduction of the FGF-BP protein.

Proliferation of the ME-180 cells was not altered by the reduction of FGF-BP, suggesting that FGF-BP is not limiting for in vitro phenotype. In addition to FGF-BP, ME-180 cells also produce bFGF, but no aFGF. Since FGF-BP can release bFGF from the extracellular matrix, the conditioned media from the ME-180 cell lines were concentrated and partially purified by heparin-affinity chromatography. Peak activities of FGF-BP elute at 1 M NaCl, whereas bFGF elutes at salt concentration of $\geq$1.5 M NaCl from heparin-Sapharose. In a bioassay, aliquots of the 1 M and 2 M elutes of ME-180 cells stimulated colony formation of SW-13 cells. FGF-BP stimulates colony formation of these cells by releasing their endogenous bFGF stored in the extracellular matrix. Addition of a neutralizing antibody to bFGF inhibited the stimulation by the 1 M and 2 M NaCl fractions, whereas a control anti-aFGF antibody showed no effect. The reduction of FGF-BP decreased the amount of stimulating activity of the 1 M as well as the 2 M fractions. Again, the treatment with the neutralizing antibodies confirmed that the stimulation was due to bFGF. This demonstrated that biologically active bFGF is released into the media of ME-180 cells (the 2 M NaCl fraction) and that this release is dependent on the production of FGF-BP. In parallel with the release of bFGF into media of FGF-BP depleted cells, cellular bFGF was increased.

One million each of different ME-180 cell lines in 0.1 ml of serum-free media were injected subcutaneously into female athymic nude mice and the tumor size measured. The tumors were surgically removed when they reached a size of 50 to 70 $mm^2$ and subsequently analyzed for FGF-BP mRNA levels with Northern analysis. Tumor growth of the ME-180 cells was reduced in parallel with the reduced levels of the FGF-BP mRNA. Even the rather small reduction of endogenous FGF-BP mRNA by only 20% using the Rz697 group resulted in a 35% reduction of the size of subcutaneous tumors one month after the injection of tumor cells. A further reduction of FGF-BP mRNA resulted in a further (81%) reduced tumor growth.

To assess whether a selection against the FGF-BP-depleted subpopulations of cells occurred in vivo, FGF-BP mRNA levels were analyzed in six different tumors in each of the three groups. For this, tumors were allowed to grow to a size of 50–70 $mm^2$. The relative mRNA levels in the tumors after in vivo growth correlated perfectly with the native mRNA levels found in the cultured tumor cells prior to their inoculation into animals. Obviously, no in vivo selection occurs. This suggests that the overall stimulus for the tumor cells towards the tumor stroma drives extension of the stroma and no individual, high-producer tumor cell will have a selection advantage in this setting.

Reduction of FGF-BP did not alter the well-differentiated morphology of the ME-180 tumors. However, a significant reduction of the number of microvessels was observed in the FGF-BP depletion tumors after highlighting endothelial cell lining with an anti-CD31 antibody.

A strong developmental regulation of FGF-BP in the intestine was observed, and the gene product expression in colon cancer was found in cell lines and samples. To assess whether the findings on the role of FGF-BP in SCC cells may also be valid for FGF-BP-positive colon cancer cells, LS174T cells were used as a model. From these highly tumorigenic cells several derivative cell lines were stably transfected with the empty control vector or with a ribozyme expression vector for Rz332. In the in vitro characterization of the cells, it was found that ribozyme transfection reduced the FGF-BP mRNA levels by 70% and the amount of secreted FGF-BP protein by 60%, but that this did not affect proliferation of the cells in culture. In the study, the LS174T cells were stably transfected with the empty vector or the Rz332 vector and analyzed for FGF-BP mRNA and secreted protein. The tumor xenograft studies in these animals showed a significant reduction of the growth (by 60%, p<0.001) and of tumor angiogenesis by 23.1±11.3% (n=4 blinded observers, p<0.05) of the FGF-BP-reduced colon cancer cells. These results have been reproduced in a second independent study with a further ribozyme-transfected and FGF-BP-reduced LS174T derivative cell line (LS174T/Rz332-1).

It was previously known that FGF-BP is expressed in SCC cell lines from different organs and that at very high levels in almost all SCC tumor tissue specimen from patients. This gene product also was found in some colon cancer samples and cell lines. In contrast, normal adult tissues did not appear to express FGF-BP mRNA, as evidenced by Northern blotting. It was observed that FGF-BP expression is up-regulated transcriptionally by the phorbolester TPA in cultured cells and increased dramatically in the final stages of carcinogen-induced skin tumors in mice as well as in carcinogen-treated skin grafted onto SCID mice.

The genetic approach of ribozyme-targeting to down-regulate spontaneous expression of FGF-BP mRNA as taught herein is an appropriate means of decreasing tumor growth and angiogenesis. The ribozymes of the invention may be administered using viral or non-viral transfer vectors. Synthetic ribozymes may also be administered. The ribozymes in pharmaceutically acceptable carrier may be administered in any manner that will result in contacting the malignant cells, including, for example, intravenous, intra-arterial, intra-ocular, intranasal, transvaginal, topical, intrathecal, intraperitoneal and subcutaneous administration. Compositions containing the ribozymes may be administered directly into the tumor or into the arterial blood supply to the tumor.

The ribozymes of the invention may be administered in means known for the administration of oligonucleotides such as in viral expression vectors or in liposomes.

The antisense oligonucleotides can be phosphorothioated and then encapsulated in liposomes such as those disclosed in WO 95/11670. The preferred liposomes for this purpose are multilamellar having a solute entrapped in its aqueous compartments. The following is an example of means for making such liposomal compositions.

Distearoyl phosphatidylcholine (DSPC), cholesterol and dimethyldioctadecylammonium bromide (DDAB) liposomes (50 mole percent DSPC, 40 mole percent cholesterol and 10 mole percent DDAB) are prepared by dissolving 3.59 mg DSPC, 1.54 mg cholesterol and 0.631 mg DDAB in methanol in a 100 ml round-bottom flask. HEPES buffer (10 mM HEPES, 150 mM NaCl) is added to the flask and the sample is roto-evaporated to remove organic solvent. An additional 5 ml HEPES buffer is added to the flask, which is then heated to 65° C. The dried film is hydrated over night with 4 mg oligonucelotides of the invention in 4 ml HEPES buffer under refrigeration. The film is dispersed by centrifugation at 20,000 rpm for 20 minutes followed by sonication. The liposomes may then be frozen and rethawed several times to produce multilamellar vesicles.

What we claim is:

1. A method of inhibiting expression of fibroblast growth factor binding protein (FGF-BP) in a cell in vitro by administration of FGF-BP ribozymes which cleave FGF-BP mRNA, wherein said ribozymes are hammerhead ribozymes as depicted in (FIG. 1) having a target cleavage site selected from the group consisting of 258, 332 and 697 nucleotides downstream of the translation initiation site of FGF-BP mRNA, and wherein said ribozymes comprise antisense sequences 5' and 3' to the ribozyme catalytic center that direct the ribozymes to said target cleavage site, such that expression of FGF-BP is inhibited.

2. A method of claim 1 wherein the ribozymes are administered in the form of liposomes.

3. A method of claim 1 wherein the ribozymes are administered in viral vectors.

4. A composition comprising ribozymes which specifically cleave FGF-BP mRNA, wherein said ribozymes are hammerhead ribozymes as depicted in (FIG. 1) having a target cleavage site selected from the group consisting of 258, 332, and 697 nucleotides downstream of the translation initiation site of FGF-BP mRNA, and wherein said ribozymes comprise antisense sequences 5' and 3' to the ribozyme catalytic center that direct the ribozymes to said target cleavage site.

5. The composition of claim 4, wherein said ribozymes are comprised in liposomes.

6. The method of claim 1, wherein said ribozymes are in a pharmaceutically acceptable carrier.

7. The method of claim 1, wherein said FGF-BP is encoded by the DNA sequence of SEQ ID NO: 1.

8. The method of claim 1, wherein said 5' and 3' antisense sequences together are 8 to 30 nucleotides long.

9. The method of claim 8, wherein said antisense sequences are selected from the group consisting of SEQ ID NO: 2, SEQ ID NO: 3, SEQ ID NO: 4 and SEQ ID NO: 5.

10. The composition of claim 4, wherein said ribozymes are in a pharmaceutically acceptable carrier.

11. The composition of claim 9, wherein said FGF-BP is encoded by the DNA sequence of SEQ ID NO: 1.

12. The composition of claim 4, wherein said 5' and 3' antisense sequences are together at least 8 to 30 nucleotides long.

13. The composition of claim 12, wherein said antisense sequences are selected from the group consisting of SEQ ID NO: 2, SEQ ID NO: 3, SEQ ID NO: 4 and SEQ ID NO: 5.

14. A method for reducing tumor growth by reducing the expression of FGF-BP mRNA in said tumor, comprising administration of the composition of claim 4, 10, 11 12, or 13, wherein said composition is injected directly into the tumor, such that the growth of said tumor is reduced.

* * * * *